United States Patent
Danby

Patent Number: 5,964,583
Date of Patent: Oct. 12, 1999

[54] ELASTOMERICALLY ASSISTED PERISTALTIC PUMP

[75] Inventor: Hal C. Danby, Nr. Sudbury, United Kingdom

[73] Assignee: Baxter International Inc., Deerfield, Ill.

[21] Appl. No.: 08/950,466

[22] Filed: Oct. 15, 1997

[51] Int. Cl.⁶ .................................................. F04B 45/06
[52] U.S. Cl. ........................................... 417/474; 604/153
[58] Field of Search ................................ 417/474, 477.9, 417/477.12, 479; 604/153

[56] References Cited

U.S. PATENT DOCUMENTS

| | | | |
|---|---|---|---|
| 1,765,360 | 6/1930 | Baumann | 417/477.7 |
| 4,080,113 | 3/1978 | Lechat et al. | 417/476 |
| 4,479,797 | 10/1984 | Kobayashi et al. | 604/153 |
| 4,482,347 | 11/1984 | Borsanyi | 604/153 |
| 4,586,882 | 5/1986 | Tseng | 417/477.3 |
| 4,671,792 | 6/1987 | Borsanyi | 604/153 |
| 4,936,760 | 6/1990 | Williams | 417/479 |
| 5,024,586 | 6/1991 | Meiri | 417/477.7 |
| 5,039,279 | 8/1991 | Natwick et al. | 417/63 |
| 5,165,873 | 11/1992 | Meijer | 417/474 |
| 5,215,450 | 6/1993 | Tamari | 417/474 |
| 5,290,158 | 3/1994 | Okada | 417/474 |
| 5,468,129 | 11/1995 | Sunden et al. | 417/477.12 |
| 5,674,052 | 10/1997 | Berra | 417/53 |

*Primary Examiner*—Charles G. Freay
*Assistant Examiner*—Robert Z. Evora
*Attorney, Agent, or Firm*—Thomas D. Bratschun; Francis C. Kowalik

[57] ABSTRACT

A liquid delivery device which controls the flow of liquid from a liquid reservoir includes a resilient tubing having a wall with a substantially cylindrical cross-section defining a flow lumen. The flow lumen is in fluid communication with the reservoir. A compression member selectively compresses a lengthwise segment of the cylindrical wall to collapse the flow lumen and releases the lengthwise segment to open the flow lumen. An elastomeric sleeve envelopes greater than half an outer diameter of the cylindrical cross-section of the resilient tubing along at least a portion of the lengthwise segment of the cylindrical wall. The elastomeric sleeve biases the lengthwise segment of the resilient tube to restore it to its substantially cylindrical cross-section when the compression member releases the lengthwise segment.

12 Claims, 2 Drawing Sheets

ELASTOMERICALLY ASSISTED PERISTALTIC PUMP

BACKGROUND OF THE INVENTION

1. Technical Field

The present invention is directed toward liquid delivery devices for controlling the flow of liquid from a liquid reservoir, and more particularly toward an improved accuracy peristaltic pump.

2. Background Art

Peristaltic pumps are particularly suited for use in accurately metering and infusing fluids such as medications into the bodies of hospital patients. Heminway, U.S. Pat. No. 4,893,991, discloses a linear type of peristaltic pump. Natwick, U.S. Pat. No. 5,055,001, discloses a valve/plunger type of peristaltic pump. Galea, U.S. Pat. No. 3,999,891, discloses a rotary type peristaltic pump. Each of these peristaltic pumps operate to propel liquid through a resilient tubing which is typically made from a flexible plastic material such as polyvinyl chloride or the like. The tubing is repeatedly compressed and expanded along a defined section of the tubing. The tube is typically expanded or "rebounded" by its internal resiliency. A known problem with this type of pump is that the portions of tubing which are intermittently compressed and expanded tend to fatigue with time. As a result, the tubing is less able to rebound to its original cross-section when released, decreasing the volume of the tubing along the critical pump segment and thereby degrading pump accuracy. U.S. Pat. No. 4,893,991 notes that such pumps have been found to exhibit as much as a 10% drop in flow rate in a 24 hour period.

The prior art has recognized this short coming in peristaltic pumps and has attempted at least three ways to solve the problem. First, Heminway, U.S. Pat. No. 4,893,991, attempts to improve pump accuracy by preventing the portion of resilient tubing which is subject to compression and expansion from assuming a cylindrical configuration upon expansion. That is, the plungers which compress and expand the tubing are designed to maintain the segment of tubing in an oval cross-section even at full expansion. A principal problem with the solution set forth in Heminway is that it requires very accurate tolerances with the plungers in the retracted position so that the tubing expands to a consistent oval cross-section in order for the pump to operate at accurate rates and volumes. In addition, because the tubing is not able to assume its full circular cross-section, and therefore its greatest volume, Heminway unduly restricts the rate liquid can be pumped.

Natwick, U.S. Pat. No. 5,055,001, proposes an even more complicated solution to improving accuracy in peristaltic pumps. Natwick proposes that the range of diametric compression of the tubing be from about 15% with the plunger retracted to about 85% with the plunger extended. Natwick argues that since the tubing need never recover to a fully uncompressed condition, changes in the elasticity of the flexible tubing due to continued use and repeated compression have much less effect on the volumetric capacity of the pump. In addition, because the plunger never fully compresses the pumping portion of the tubing, the tubing is subjected to less fatigue. Natwick further teaches providing mechanical tubing shapers disposed on each side of the plunger which are extended to reform the pumping portion of the tubing as the plunger is retracted and the tubing refills with fluid. Natwick suffers from the same shortfall of Heminway in that it restricts the volume of the tubing used for pumping and therefore limits pump output rates. In addition, the tubing shapers are complex mechanical structures which create an additional avenue for potential pump failure. Moreover, the mechanical shapers taught in Natwick require a number of potentially costly parts and complicate the assembly of the pump.

Mannes, U.S. Pat. No. 4,585,442, discloses an intravenous infusion rate controller which operates on a resilient tubing which rests in a trough between a pair of resilient bands. The resilient bands act on opposing sides of the outer diameter of the tubing in a compressed state to aid in restoring the tube to its original cross-section upon expansion. In this manner the resilient bands inhibit the tendency of the tube to "flatten out" and rebound to only an oval cross-section which degrades the accuracy of the rate controller. Unfortunately, the resilient bands act on only two discrete points in attempting to restore the tubing to its original shape. Moreover, the space between the resilient bands must be maintained at rather precise tolerances to avoid the resilient bands compressing the tubing into an oval cross-section if the bands are too close or failing to restore the tube to its circular cross-section if the bands are too far apart.

The present invention is directed toward overcoming one or more of the problems discussed above.

SUMMARY OF THE INVENTION

A first aspect of the invention is a liquid delivery device which controls the flow of liquid from a liquid reservoir. The liquid delivery device includes a resilient tubing having a wall with a substantially cylindrical cross-section defining a flow lumen. The flow lumen is in fluid communication with the reservoir. A compression member selectively compresses a lengthwise segment of the cylindrical wall to collapse the flow lumen and releases the lengthwise segment to open the flow lumen. An elastomeric sleeve envelopes greater than half an outer diameter of the cylindrical cross-section of the resilient tubing along at least a portion of the lengthwise segment of the cylindrical wall. The elastomeric sleeve biases the lengthwise segment of the resilient tube to restore it to its substantially cylindrical cross-section when the compression member releases the lengthwise segment.

The elastomeric sleeve, in a relaxed state, has an inner diameter less than an outer diameter of the resilient tubing. The elastomeric sleeve further has a lengthwise substantially linear opening along less than half the cross-section of the sleeve so that a portion of the resilient tubing can be received lengthwise within the elastomeric sleeve with more than half the diameter of the tubing cross-section enveloped by the sleeve. As the lengthwise segment of the resilient tube is collapsed, the opening of the elastomeric sleeve expands to release the lengthwise segment of the tube. The liquid delivery device preferably further includes an integral handle along the length of the elastomeric sleeve and a clamp for grasping the handle to fix the position of the elastomeric sleeve relative to the compression member.

A second aspect of the invention is a peristaltic pump for delivering a flow of liquid from a reservoir through elongate resilient tubing. The resilient tubing has a wall with a substantially cylindrical cross-section defining a flow lumen. The flow lumen is in fluid communication with the reservoir. The peristaltic pump comprises an elongate elastomeric sleeve which, in a relaxed state, has an inner diameter less than an outer diameter resilient tubing. The elastomeric sleeve has a lengthwise substantially linear opening along less than half of the cross-section of the sleeve so that a portion of the resilient tubing can be received lengthwise within the elastomeric sleeve with more than half the diameter of the tubing cross-section enveloped by the sleeve. A plurality of spaced reciprocating plungers are arranged substantially linearly along the elastomeric sleeve. The reciprocating plungers extend and retract relative to the elastomeric sleeve. An anvil is disposed opposite each of the plurality of plungers, adjacent the opening of the elastomeric sleeve and spaced from the plungers so that, with the resilient tubing received in the elastomeric sleeve, the reciprocating plungers collapse the flow lumen against the anvil with the plungers extended and do not collapse the flow lumen with the plungers retracted. As the plungers are retracted so as to no longer collapse the flow lumen, the elastomeric sleeve biases the resilient tubing received therein to its substantially cylindrical cross-section. As the segment of the resilient tubing is collapsed, the opening of the elastomeric sleeve expands to release the resilient tubing and the resilient tubing is in direct contact with the anvil. The elastomeric sleeve preferably includes an integral handle along its length and the peristaltic pump preferably includes a clamp for grasping the handle to fix the position of the elastomeric sleeve relative to the plungers. The resilient tube may be held in position relative to the plungers and anvil substantially solely by the elastomeric sleeve.

In a preferred embodiment, the elastomeric sleeve, in cross-section, is an extended semi-circle with a lengthwise handle extending along each end of the extended semi-circle and the peristaltic pump includes clamps for grasping the handles to fix the position of the elastomeric sleeve relative to the plungers.

A third aspect of the present invention is an elastomeric sleeve for use in a liquid delivery device. The liquid delivery device controls the flow of liquid from a liquid reservoir through a resilient tubing by a compression member selectively compressing and releasing a lengthwise segment of the tubing to collapse and restore a lumen of the tubing. The elastomeric sleeve consists of an elongate side wall which, in a relaxed state, has an inner diameter slightly less than an outer diameter of the resilient tubing and a lengthwise substantially linear opening of a width less than half the cross section of the side wall. A lengthwise handle extends from the side wall. The side wall and the handle are integrally formed of a single piece of elastomer.

The elastomeric sleeve of the present invention subjects the majority of the wall of resilient tubing to a uniform compression which serves to bias and restore the tubing to its substantially its circular cross-section. In this manner, the segment of tubing subject to compression and expansion pumps liquid at a constant rate over extended periods of time. In addition, the sleeve helps secure the tubing in a desired position relative to the compression member or plunger and anvil to ease loading of the tubing into the pumping device and to help secure the tubing during pumping. The elongate opening in the sleeve expands during compression of the tubing segment so that the tubing directly connects the anvil, which causes compression of the tubing between the rigid anvil and the plunger. This decreases the amount of energy necessary to collapse the lumen (as opposed to having to compress the entire elastomeric sleeve between the plunger and anvil), thereby improving pumping efficiency. Furthermore, the sleeve is readily manufactured out of inexpensive materials and is easy to instal.

DETAILED DESCRIPTION OF THE PREFERRED EMBODIMENT

Figure 1:
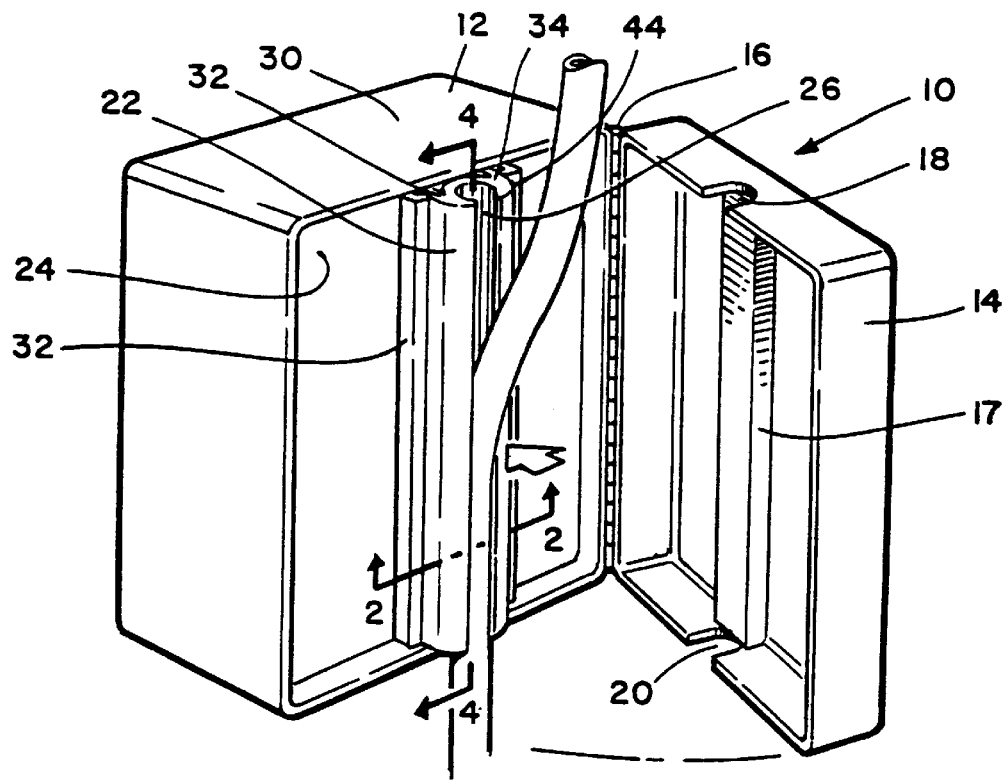
FIG. 1 is a perspective view of a peristaltic pump housing including an elastomeric sleeve in accordance with the present invention.

An improved accuracy peristaltic pump 10 is shown in perspective view in FIG. 1. Most of the features not important to the understanding of this invention such as controls, latch mechanisms and the like have been omitted for the sake of clarity. The improved accuracy peristaltic pump 10 includes a housing base 12 and a housing door 14 joined by a hinge 16. An anvil 17 is attached to an inner surface of the housing door 14 and runs lengthwise of the door 14. The door 14 further includes a pair of annular slots 18, 20 in its top and bottom side walls. While the specific embodiment disclosed herein is of a peristaltic type pump, the elastomeric sleeve can also provide its many advantages in other flow control devices such as the intravenous infusion rate controller disclosed in Mannes, U.S. Pat. No. 4,585,442, the disclosure of which is hereby incorporated by reference.

Figures 2, 3:
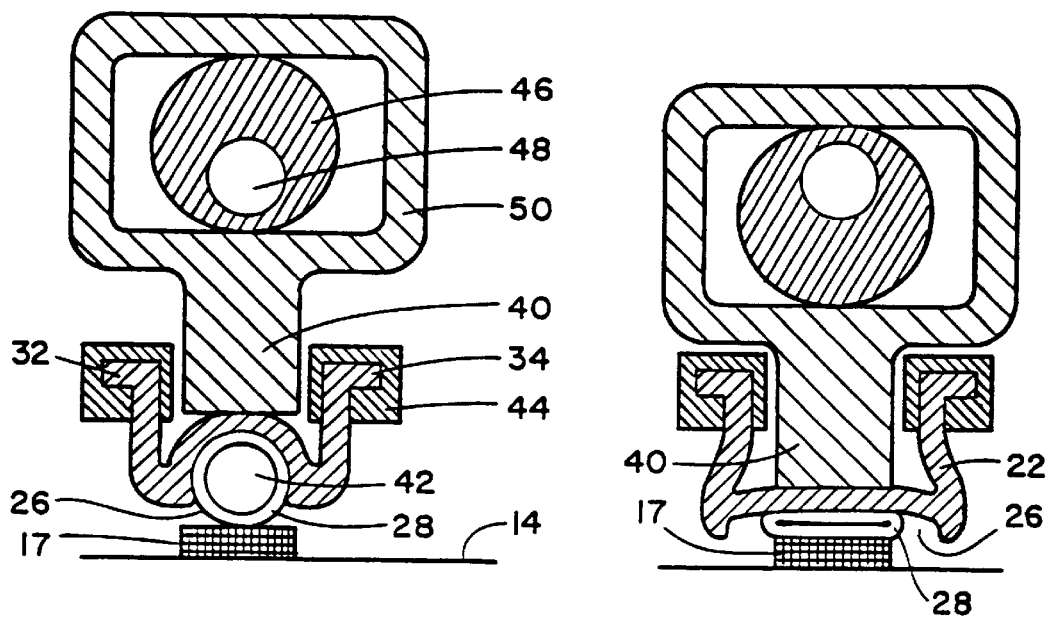
FIG. 2 is a cross-sectional view taken along line 2—2 of FIG. 1 with the pump housing door shut and a plunger in a retracted position.
FIG. 3 is the same as FIG. 2 only the plunger is shown in an extended position.

An elastomeric sleeve 22 is attached to a partition 24 within the housing base 12 and runs the length of the housing base 12. The elastomeric sleeve 22 is positioned relative to the anvil 17 so that with the door 14 closed, the surface of the anvil 17 aligns with an elongate opening 26 of the elastomeric sleeve 22. As seen in FIGS. 1 and 2, the elastomeric sleeve 22 consists of a substantially cylindrical side wall 30 with the lengthwise opening 26 removed from the side wall. A pair of handles 32, 34 extend lengthwise along the elastomeric sleeve 22 and project tangentially from adjacent the lengthwise slot 26. Referring to FIG. 2, the elastomeric sleeve in cross-section is an extended semi-circle with each handle 32, 34 extending tangentially along each end of the semi-circle. The elastomeric sleeve 22, including the handles 32, 34 is integrally formed of a single piece of a suitable resilient, deformable elastomer, such as rubber, preferably a room temperature vulcanizing (RTV) silicone.

The elastomeric sleeve 22 is dimensioned so that the inner diameter of the cylindrical side wall is slightly smaller than the outer diameter of the resilient tubing 28. In addition, the width of the elongate slot 26 is less than one half the cross-section of the elastomeric sleeve 22. In this manner, as the resilient tubing 28 is installed as illustrated in Fig. 1, the resilient tubing 28 is held in place. As best shown in FIG. 2, the elastomeric sleeve 22 biases the resilient tubing 28 to restore it to a substantially circular cross-sectional shape wherein the flow lumen 42 is unrestricted and the plunger 40 is restricted. Referring to FIG. 2 and as shown with regard to the handle 34 in FIG. 1, the handles 32, 34 are secured by elongate clamps 44.

As seen in FIG. 2, the plunger 40 is actuated by a cam 46 mounted eccentrically to a drive shaft 48, the cam residing in a collar 50 attached to the plunger 40. In FIG. 2 the plunger is in a retracted position. The plunger 40 is illustrated in its fully extended position in FIG. 3. Here the plunger 40 is shown having fully collapsed the lumen 42 of the resilient tubing 28. In addition, the plunger 40 causes the elongate slot 26 to expand and release the tubing 28. In this manner, the tubing 28 is compressed directly against the anvil 17 as it is disengaged from the elastomeric sleeve 22.

Figure 4:
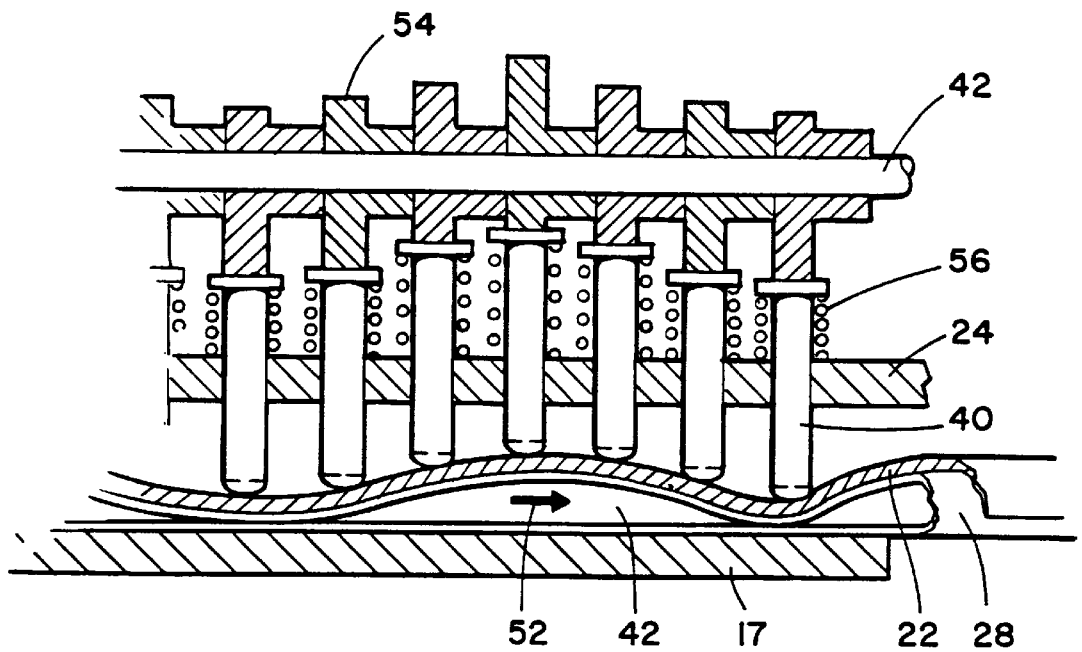
FIG. 4 is a cross-sectional view taken along line 4—4 of FIG. 1 showing the elastomeric sleeve and resilient tubing operatively associated with the linear peristaltic pump apparatus.

In FIG. 4 the door 14 is closed and the resilient tubing 28 and the sleeve 22 are in an operative position relative to the anvil 17 and plungers 40. The plungers 40 are sequentially extended and retracted relative to the tubing 28 and elastomeric sleeve 22 to propel fluid through the lumen 42 as indicated by the arrow 52. The operation of a linear peristaltic pump as illustrated FIG. 4 is described in detail in Heminway, U.S. Pat. No. 4,893,991, the disclosure of which is incorporated herein by reference. The plunger mechanism illustrated in FIG. 4 differs from that illustrated in FIGS. 2 and 3 in that instead of having eccentric cams 54 mounted within a collar 50 to direct the plunger between its extended and retracted position, springs 56 bias the plungers toward a retracted position and the eccentric cams 54 extend the plungers 40 as they rotate around the drive shaft 42.

Figure 5:
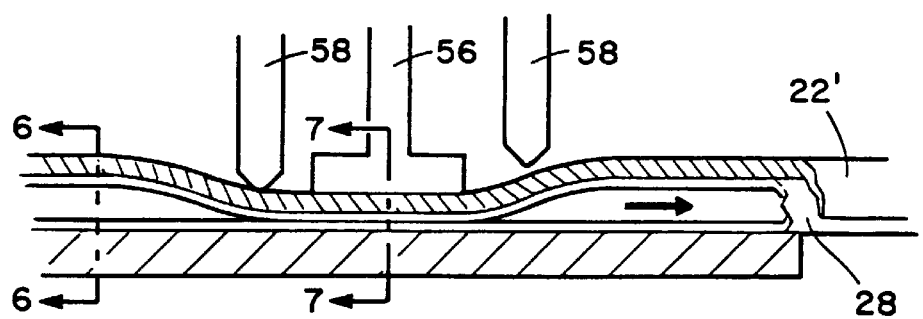
FIG. 5 is an alternate embodiment of FIG. 4 showing a valve/plunger of a peristaltic pump replacing the linear peristaltic pump of FIG. 4 and with an alternate embodiment of the elastomeric sleeve.
Figures 6, 7:
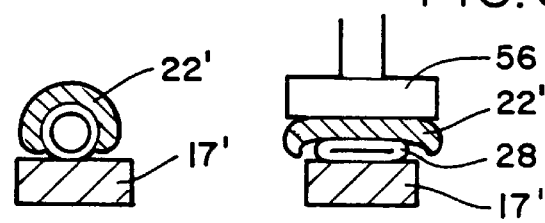
FIG. 6 is a cross-sectional view taken along line 6—6 of FIG. 5.
FIG. 7 is a cross-sectional view taken along line 7—7 of FIG. 5.

FIG. 5 illustrates another embodiment of the elastomeric sleeve 22 used in conjunction with a valve/plunger type peristaltic pump. The elastomeric sleeve 22' does not include the elongate handles 32, 34, but is in all other manners identical to the elastomeric sleeve 22 described above with regard to FIGS. 1–4. In this embodiment the resilient tubing 28 resides within the elastomeric sleeve 22' and is held in place by a length of the elastomeric sleeve 22' which is not subjected to compression, as illustrated in FIG. 6. When subject to compression, just as described above with regard to FIG. 3, the elastomeric sleeve 22' disengages the resilient tubing 28 so it may be compressed directly against the anvil 17'. Because of the absence of the lengthwise handles 32, 34, the sleeve 22' must be secured to the housing in some other manner. For example, the ends of the sleeve may be fastened to the housing. Also, although not illustrated in FIG. 5, the elastomeric sleeve 22' need not extend continuously between the plunger 56 and the valves 58. The elastomeric sleeve need only extend along a portion of the tubing subject to compression a distance sufficient to restore the portion of tubing back to the substantially cylindrical cross-section.

The improved accuracy peristaltic pump features an elastomeric sleeve which envelopes greater than half of the outer diameter of a resilient tubing to bias the tubing to a substantially cylindrical cross-section in a relaxed state. By providing substantially uniform compression about the periphery of the resilient tubing, the resilient tubing is reliably repeatedly restored to the substantially cylindrical shape. Thus, the elastomeric sleeve insures the continued accuracy of a liquid delivery device such as a peristaltic pump that controls fluid flow by repeated compression and release of a resilient tubing. The elastomeric sleeve also secures the resilient tubing which both assists in retaining the resilient tubing in an operative position relative to the plunger and anvil and also provides a convenient way for insuring the tube is properly loaded in the pump housing prior to a fluid delivery operation. Because the sleeve releases the tubing during extension of the plunger, the tubing is compressed directly against the anvil 17, minimizing energy consumption by the pump. Moreover, these many advantages are provided by an elastomeric sleeve that is inexpensively fabricated out of a variety of elastomers and installed in a pump for minimal cost.

What is claimed is:

1. A liquid delivery device for controlling the flow of liquid from a liquid reservoir, the liquid delivery device comprising:
   a resilient tubing having a wall with a substantially cylindrical cross-section defining a flow lumen, the flow lumen being in fluid communication with the reservoir;
   a compression member selectively compressing a lengthwise segment of the cylindrical wall to collapse the flow lumen and releasing the lengthwise segment to open the flow lumen; and
   an elastomeric sleeve enveloping greater than half an outer diameter of the cross-section of the resilient tubing along at least a portion of the lengthwise segment of the cylindrical wall, the elastomeric sleeve biasing the lengthwise segment of the resilient tube to its substantially cylindrical cross-section when the compression member releases the lengthwise segment.

2. The liquid delivery device of claim 1 wherein the elastomeric sleeve, in a relaxed state, has an inner diameter less than an outer diameter of the resilient tubing, the elastomeric sleeve further having a lengthwise substantially linear opening of a width along less than half the cross-section of the sleeve so that a portion of the resilient tubing can be received lengthwise within the elastomeric sleeve with more than half the diameter of the tubing cross-section enveloped by the sleeve.

3. The liquid delivery device of claim 2 wherein the lengthwise opening is of a width sufficient that as the lengthwise segment of the resilient tubing is collapsed, the lengthwise opening expands to release the lengthwise segment of the resilient tubing.

4. The liquid delivery device of claim 1 further comprising an integral handle along the length of the elastomeric sleeve and means for grasping the handle to fix the position of the elastomeric sleeve relative to the compression member.

5. A peristaltic pump for delivering a flow of liquid from a reservoir through an elongate resilient tubing having a wall with a substantially cylindrical cross-section defining a flow lumen, the flow lumen being in fluid communication with the reservoir, the peristaltic pump comprising:
   an elongate elastomeric sleeve which, in a relaxed state, has an inner diameter less than an outer diameter of the elongate resilient tubing, the elastomeric sleeve having a lengthwise substantially linear opening of a width less than half the cross-section of the sleeve so that a portion of the resilient tubing can be received lengthwise within the elastomeric sleeve with more than half the diameter of the tubing cross-section enveloped by the sleeve;
   a plurality of spaced reciprocating plungers arranged substantially linearly along the elastomeric sleeve, the reciprocating plungers extending and retracting relative to the elastomeric sleeve;
   an anvil disposed opposite each of the plurality of plungers, adjacent the linear opening of the elastomeric sleeve and spaced from the plungers so that, with the resilient tubing received in the elastomeric sleeve, the reciprocating plungers collapse the flow lumen against the anvil with the plungers extended and do not collapse the flow lumen with the plungers retracted,
   whereby as the plungers are retracted so as to no longer collapse the flow lumen, the elastomeric sleeve biases the resilient tubing received therein to its substantially cylindrical cross-section.

6. The peristaltic pump of claim 5 wherein the lengthwise opening is of a width sufficient that as the lengthwise segment of the resilient tubing is collapsed, the lengthwise opening expands to release the resilient tubing and the resilient tubing is in direct contact with the anvil.

7. The peristaltic pump of claim 5 further comprising an integral handle along the length of the elastomeric sleeve and means for grasping the handle to fix the position of the elastomeric sleeve relative to the plungers.

8. The peristaltic pump of claim 7 wherein the resilient tubing is held in position relative to the plungers and anvil substantially solely by the elastomeric sleeve.

9. The peristaltic pump of claim 5 wherein the elastomeric sleeve, in cross-section, is an extended semi-circle with a length-wise handle extending tangentially along each end of the extended semi-circle, the peristaltic pump further comprising means for grasping the handles to fix the position of the elastomeric sleeve relative to the plungers.

10. An elastomeric sleeve for use in a liquid delivery device which controls the flow of liquid from a liquid reservoir through a resilient tubing by a compression member selectively compressing and releasing a lengthwise segment of the tubing to collapse and restore a flow lumen of the tubing, the elastomeric sleeve comprising:

an elongate side wall which, in a relaxed state, has an inner diameter slightly less than an outer diameter of the resilient tubing and a lengthwise substantially linear opening of a width less than half the cross-section of the side wall; and a lengthwise handle extending from the side wall.

11. The elastomeric sleeve of claim 10 wherein the side wall and the handle are integrally formed of a single piece of elastomer.

12. The elastomeric sleeve of claim 10 further comprising a pair of lengthwise handles each extending tangentially from the side wall along a side of the lengthwise opening.

* * * * *